United States Patent
Bäck et al.

(10) Patent No.: US 8,439,813 B2
(45) Date of Patent: May 14, 2013

(54) METHOD OF MANUFACTURING A TOP SHEET OR BACK SHEET OF A DISPOSABLE ABSORBENT ARTICLE

(75) Inventors: Lucas Bäck, Billdal (SE); Ulrika Carlson, Billdal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 13/375,694

(22) PCT Filed: Jun. 4, 2009

(86) PCT No.: PCT/SE2009/050672
§ 371 (c)(1),
(2), (4) Date: Dec. 1, 2011

(87) PCT Pub. No.: WO2010/140942
PCT Pub. Date: Dec. 9, 2010

(65) Prior Publication Data
US 2012/0071309 A1    Mar. 22, 2012

(51) Int. Cl.
*B31B 49/00* (2006.01)
(52) U.S. Cl.
USPC ............... 493/379; 156/204; 2/400
(58) Field of Classification Search ........... 493/379; 156/204; 2/400
See application file for complete search history.

(56) References Cited

U.S. PATENT DOCUMENTS

| | | | |
|---|---|---|---|
| 4,760,764 A | 8/1988 | DeJonckheere et al. | |
| 5,034,007 A | 7/1991 | Igaue et al. | |
| 5,176,670 A * | 1/1993 | Roessler et al. | 604/391 |
| 5,695,846 A | 12/1997 | Lange et al. | |
| 5,725,714 A | 3/1998 | Fujioka et al. | |
| 5,985,081 A | 11/1999 | Reynolds | |
| 6,098,557 A * | 8/2000 | Couillard et al. | 112/475.06 |
| 6,494,872 B1 | 12/2002 | Suzuki et al. | |
| 6,508,797 B1 * | 1/2003 | Pozniak et al. | 604/385.11 |
| 6,827,804 B2 * | 12/2004 | Otsubo et al. | 156/161 |
| 7,407,496 B2 | 8/2008 | Petersen | |

FOREIGN PATENT DOCUMENTS

| | | |
|---|---|---|
| EP | 0 539 032 | 12/1996 |
| EP | 0768073 | 4/1997 |
| FR | 2 644 694 | 9/1990 |

* cited by examiner

*Primary Examiner* — Thanh Truong
(74) *Attorney, Agent, or Firm* — Drinker Biddle & Reath LLP

(57) ABSTRACT

A method of manufacturing a top sheet material or back sheet material for use in the manufacture of disposable absorbent articles including the steps of: a) splitting a continuous first web of sheet material having substantially straight side edges into a second and third continuous web by an alternating concave-convex cutting line cut in a longitudinal direction along the continuous first web, the cutting line being distanced from both side edges of the continuous first web; b) shifting the second continuous web in a lateral direction in relation to the third continuous web so that the substantially straight edges of the second and third continuous webs are parallel to and adjacent to each other and longitudinally shifting the second continuous web so that the series of concave edge portions and the series of convex edge portions of the second and third continuous webs are longitudinally aligned with each other; c) directly or indirectly joining the substantially straight edges of the second and third continuous webs to each other, thereby forming a composite fourth web. The cutting line is made in the first continuous web so that all portions of the cutting line are distanced from a longitudinal center line of the first continuous web.

9 Claims, 3 Drawing Sheets

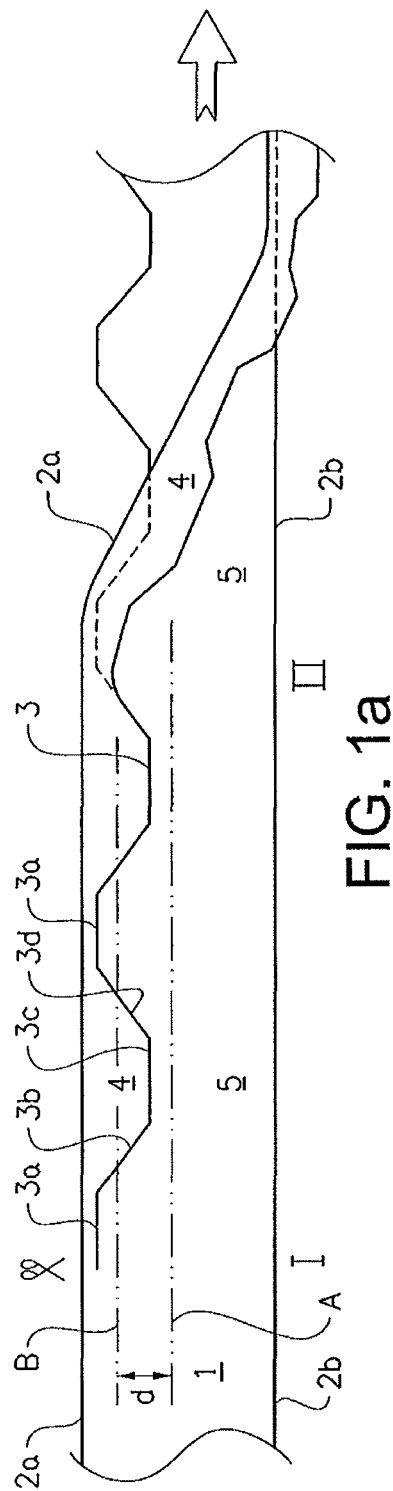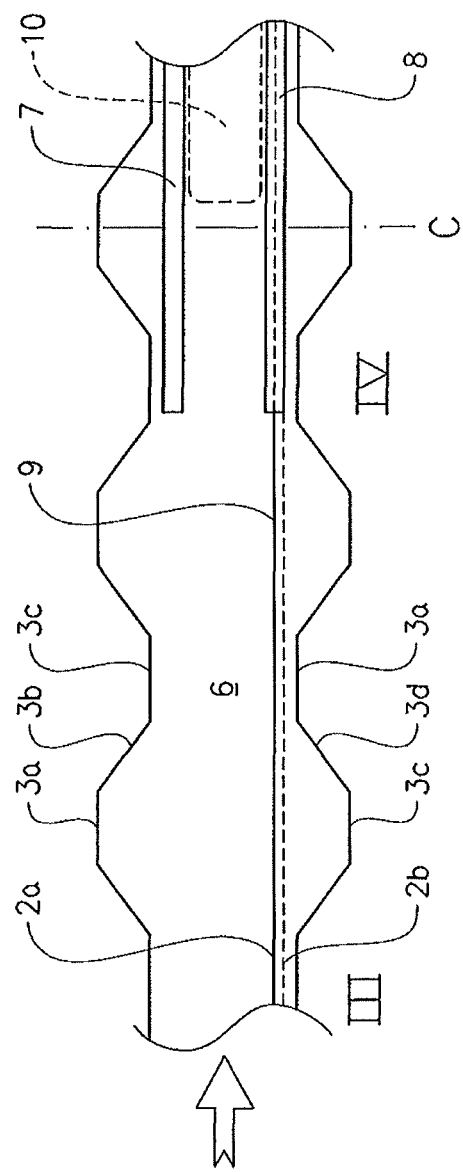
FIG. 1a
FIG. 1b

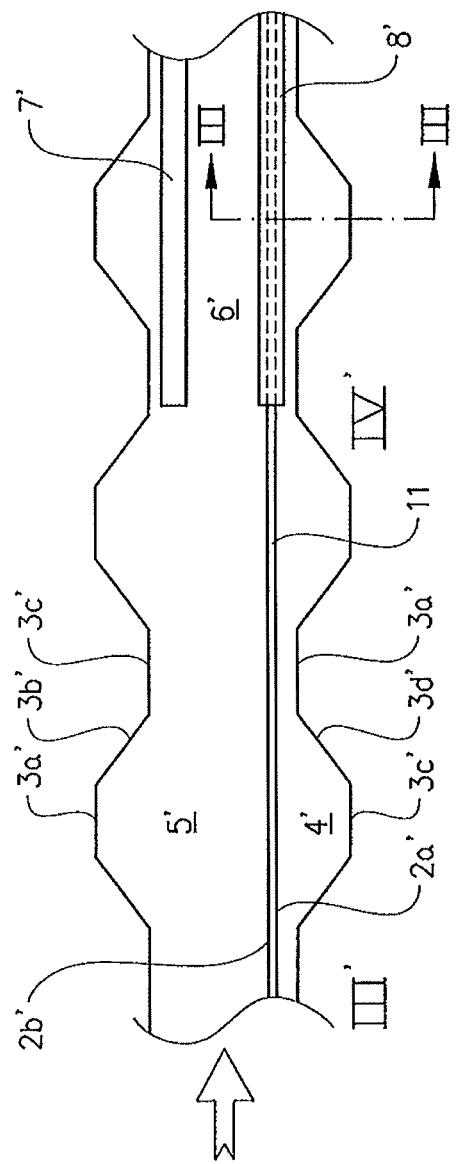
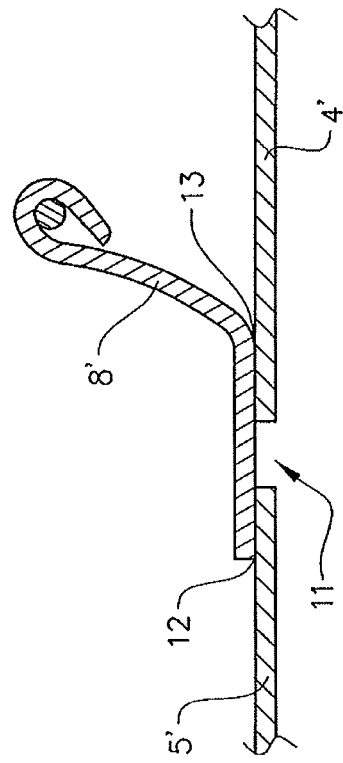
FIG. 2
FIG. 3

METHOD OF MANUFACTURING A TOP SHEET OR BACK SHEET OF A DISPOSABLE ABSORBENT ARTICLE

CROSS-REFERENCE TO PRIOR APPLICATION

This application is a §371 National Stage Application of PCT International Application No. PCT/SE2009/050672 filed Jun. 4, 2009, which is incorporated herein in its entirety.

TECHNICAL FIELD

The present disclosure relates to a method of manufacturing a top sheet material or back sheet material for use in the manufacture of disposable absorbent articles. The method includes: a) splitting a continuous first web of sheet material having substantially straight side edges into a second and third continuous web by an alternating concave-convex cutting line cut in a longitudinal direction along said continuous first web, said cutting line being distanced from both side edges of said continuous first web; b) shifting the second continuous web in a lateral direction in relation to the third continuous web so that the substantially straight edges of the second and third continuous webs are parallel to and adjacent to each other and longitudinally shifting the second continuous web so that the series of concave edge portions and the series of convex edge portions of the second and third continuous webs are longitudinally aligned with each other; c) directly or indirectly joining the substantially straight edges of the second and third continuous webs to each other, thereby forming a composite fourth web.

BACKGROUND

A method as mentioned above is known from U.S. Pat. No. 5,034,007, which allows a top sheet having leg openings to be manufactured essentially without waste of top sheet material. However, by such a method a seam along the longitudinal centre line of the top sheet material will result. Such a seam is visible for the user and must therefore be carefully manufactured to have an aesthetic pleasant appearance. Furthermore, it would be desirable not to have a seam in the area of the top sheet being occupied by an absorbent body in the end product, such as a disposable diaper for babies or adults. The presence of a seam in the middle of the top sheet, i.e. the area which emitted urine is most likely to hit, could decrease the acquisition properties of the top sheet in this area and leads to an increased risk for leakage.

SUMMARY

It is desired to modify the method stated above, in which such a seam can be disposed outside the area occupied by an absorbent body in an end product using a top sheet manufactured according to said method and in which the modification of the method does not result in additional manufacturing steps.

This can be accomplished by a method of manufacturing a top sheet material or back sheet material for use in the manufacturing of disposable absorbent articles with the steps of:

a) splitting a continuous first web of sheet material having substantially straight side edges into a second and third continuous web by an alternating concave-convex cutting line cut in a longitudinal direction along said continuous first web, said cutting line being distanced from both side edges of said continuous first web;

b) shifting the second continuous web in a lateral direction in relation to the third continuous web so that the substantially straight edges of the second and third continuous webs are parallel to and adjacent to each other and longitudinally shifting the second continuous web so that the series of concave edge portions and the series of convex edge portions of the second and third continuous webs are longitudinally aligned with each other;

c) directly or indirectly joining the substantially straight edges of the second and third continuous webs to each other, thereby forming a composite fourth web.

The cutting line is made in said first continuous web so that all portions of said cutting line are distanced from a longitudinal centre line of said first continuous web. By distancing the cutting line from the longitudinal centre line of the first continuous web, the lateral dimension of the second and third web can be chosen so that the joining line will be disposed laterally outside the area of an absorbent body in the end product. Furthermore, the dimensions can be chosen to correspond to a fastening line for other components of a top sheet for disposable absorbent articles, such as standing gathers that often are disposed on such top sheets.

In a first aspect, said cutting line is formed by a series of a straight line-an outwardly inclined line-a straight line-an inwardly inclined line. In a particular embodiment, said first continuous web is made of top sheet material. Furthermore, the substantially straight edges of the second and third webs are overlapping each other after the shifting of the second web.

In a second aspect, the substantially straight edges of the second and third webs lie edge-to-edge after shifting of the second web.

In a third aspect, the substantially straight edges of the second and third webs are distanced from each other after shifting of the second web and indirectly joined to each other by a splicing strip. To advantage, the splicing strip forms part of a standing gather.

A standing gather can also be attached to the composite fourth web along the joining line between the second and third webs in the first and second aspects.

In a particular embodiment, the longitudinal centre line of the alternating concave-convex cutting line is distanced from the longitudinal centre line of the first web by 40-120 mm, preferably 60-100 mm and more preferably 70-90 mm when a top sheet material for an adult diaper is manufactured and by 40-80 mm, preferably 50-70 mm and most preferably 60 mm when a top sheet material for a baby diaper is manufactured.

BRIEF DESCRIPTION OF THE DRAWINGS

Embodiments of the invention will now be described with reference to the enclosed figures, of which;

FIGS. 1a and b schematically illustrate a manufacturing line for continuous manufacturing of a top sheet web according to a first embodiment of the invention, FIG. 2 schematically illustrates the final steps in a second embodiment of a method according to the invention, FIG. 3 discloses a sectional view along line III-III in FIG. 2, FIGS. 4a and 4b illustrate a manufacturing line for continuous manufacturing of a top sheet web according to a third embodiment of the invention, and FIG. 5 discloses a sectional view along line V-V in FIG. 4b.

DETAILED DESCRIPTION OF PREFERRED EMBODIMENTS

Figure 4A:
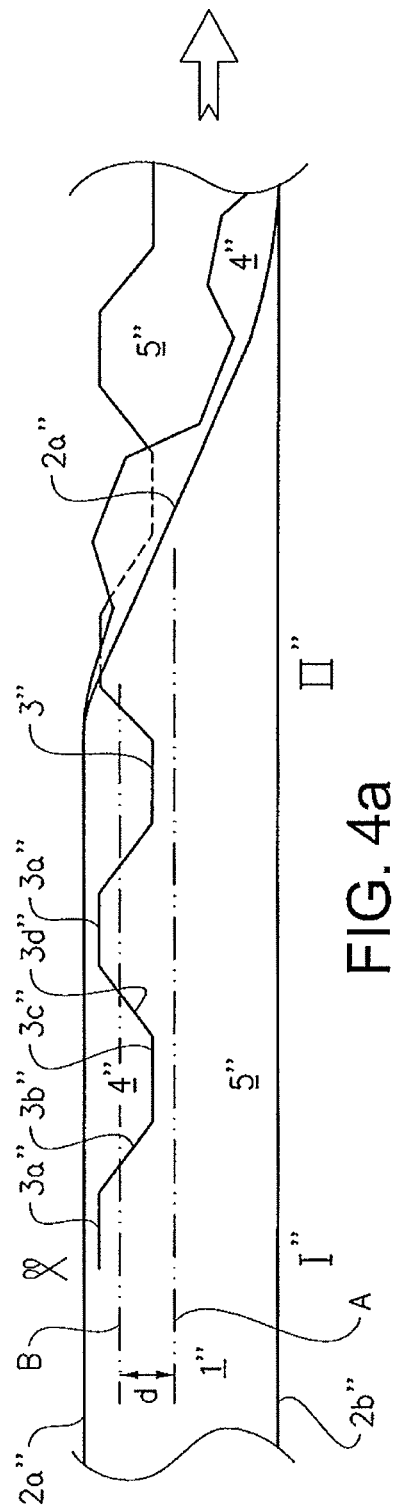

In FIG. 1a, a web 1 of top sheet material having opposite straight side edges 2a, 2b is shown in a plan view. The web 1 is disposed on suitable conveyer (not shown) and is transported thereon in a machine direction running from left to right in FIGS. 1a and 1b, as indicated by arrows in these figures.

The web 1 is fed to a cutting station I, symbolized by scissors in FIG. 1a, in which a cutting line 3 is made in the web 1. By moving the cutter in a lateral direction, i.e. a cross direction in relation to the machine direction, a series of concave-convex portions are defined by the cutting line 3. In the shown embodiment the cutting tool is moved so that a cutting line composed of a series of a straight line 3a—an inwardly inclined line 3b—a straight line 3c—an outwardly inclined line 3d is accomplished. The web 1 is thus split into a second web 4 and a third web 5 by the cutting line 3.

The split webs 4 and 5 then enters into a shifting station II. In this station web 4 is passed onto a shifting conveyer (not shown) or the like disposed above or beneath the conveyer on which web 1 and web 5 are transported. On this shifting conveyer web 4 is gradually shifted in a lateral direction until its straight side edge 2a has been moved slightly overlap the straight side edge 2b of web 5. For illustrative purposes, the lateral shifting of web 4 is exaggerated in FIG. 1a. The shifting conveyer is so dimensioned so that when the web 4 has been fully shifted it has traveled along a distance longer than the web 5 corresponding to sum of the longitudinal extensions of lines 3a and 3b when it is again in step III laid onto the same conveyer as web 5 is transported on. Thereby the convex and concave portions in the series of concave-convex portions in webs 4 and 5 formed by the cutting line 3 will coincidence as illustrated in FIG. 1b.

The shifting of web 4 can, if desired, by suitable dimensioning of the shifting conveyer take place over a longer distance in accordance with the formula that the difference in travel distances between webs 4 and 5=n×half a wave length where n=1,3,5,7 . . . and a wave length is the sum of the extensions of 3a+3b+3c+3d.

After web 4 in shifting station II has been distanced from web 5 but before web 4 is laid onto the same conveyer as web 5 with its straight side edge 2a overlapping straight side edge 2b of web 5, a glue line is applied along edge 2b on web 5 by any suitable means (not shown), such as a glue nozzle. The straight side edge portions of webs 4 and 5 are then pressed together, for example by passing the webs in the nip between two rollers, thereby bonding these webs together by a bonding line 9 and forming a fourth composite web 6 composed of webs 4 and 5.

The webs 4 and 5 can of course be joined by other suitable means than glue known to the skilled man, such as heat welding or with the aid of a ultra sound device.

In a variant of the manufacturing method, the so formed web of top sheet material is winded onto a storage roll for further use in a production line for disposable absorbent articles, such as diapers for babies or adults or incontinence guards for adults.

In a particular embodiment, the method of manufacturing a top sheet material is included as a first step in a manufacturing line for disposable absorbent articles. In such articles so called standing gathers are often present on the top sheet in order to prevent sideway leakage of liquid emitted onto the top sheet. Standing gathers are bands of elastic or elastificated material applied in an extended state to the top sheet and extending in longitudinal directions on both sides of an absorbent body in the end product. In FIG. 1b, the application of elastic bands 7,8 in an extended state is schematically illustrated. In station IV, the elastic bands 7,8 which will become standing gathers in the end product is unwinded from a storage roller (not shown) and provided with a glue string along each inner edge and thereafter pressed onto the web 6 by a pair of rollers (not shown). As is evident from FIG. 1b, the band 8 covers the bonding line 9 bonding webs 4 and 5 together as described above.

If the bonding line is accomplished by heat and pressure or with the aid of an ultrasound device, the joining of edges 2a and 2b and standing gather can occur in one step, i.e. the edges 2a, 2b and the standing gather 8 are joined together at the same time in a single joining operation.

The so formed web of top sheet material can then be laid onto another web of backsheet material (not shown) onto which a row of absorbent bodies 10 have been laid. Said web of backsheet material having such a width that its side edges coincidence with the straight portions 3c and 3a located closest to the longitudinal centre line A of web 6. The web of backsheet material is then joined to the web 6 of top sheet material in areas located outside the absorbent bodies 10 in the row of absorbent bodies. Leg elastics are also applied in an extended state between the web of backsheet material and the web of top sheet material before these webs are joined to each other.

In a last step in the production line for disposable absorbent articles the web composed of top sheet web 6, absorbent bodies 10 and web of backsheet material with bands 7 and 8 applied to the top sheet web 6 and leg elastics applied between web 6 and the web of backsheet material is cut so that individual diapers are produced. The location of one such cut is shown in FIG. 1b by dash dotted line C for illustrative purpose only.

Instead of laying the top sheet web 6 onto a web including a row of absorbent bodies thereon, the row of absorbent bodies can be laid onto the top sheet web 6 and the web of backsheet material can then be laid onto the top sheet web 6 and be joined thereto. If standing gathers are to be applied to the top sheet this should then be done on the side of the top sheet web opposite to the side onto which absorbent bodies are or are to be laid.

In FIGS. 2 and 3, a second embodiment is schematically illustrated. The first steps I and II of the method are the same as described with reference to FIG. 1a, the only difference being that web 4' is shifted in the lateral direction to such extent that a gap 11 exists between edges 2a' and 2b' when the web 4' in step III' is laid back onto the same conveyer as web 5'. The components in the second embodiment corresponding to similar components in FIGS. 1a and 1b are given the same reference numerals with the addition of a prime sign. In the second embodiment web 5' and web 4' are indirectly joined together by both being affixed to the lower side of standing gather 8', such bonds being indicated by 12 and 13 in FIG. 3. If the composite sheet is not intended to be provided with a standing gather a splicing strip could be used instead. By the use of a splicing strip, which can be in the form of a standing gather, for indirect joining together the edges of webs 4',5' the required accuracy of the lateral shifting of web 4' is reduced. Furthermore, the edges 2a',2b' of the webs 4',5' need not be perfectly straight but irregularities from perfect straightness can be allowed.

A splicing strip for indirect joining of edges 2a',2b' of webs 4',5' can be preferably made of the same type of material as webs 4',5'.

Figure 4B:
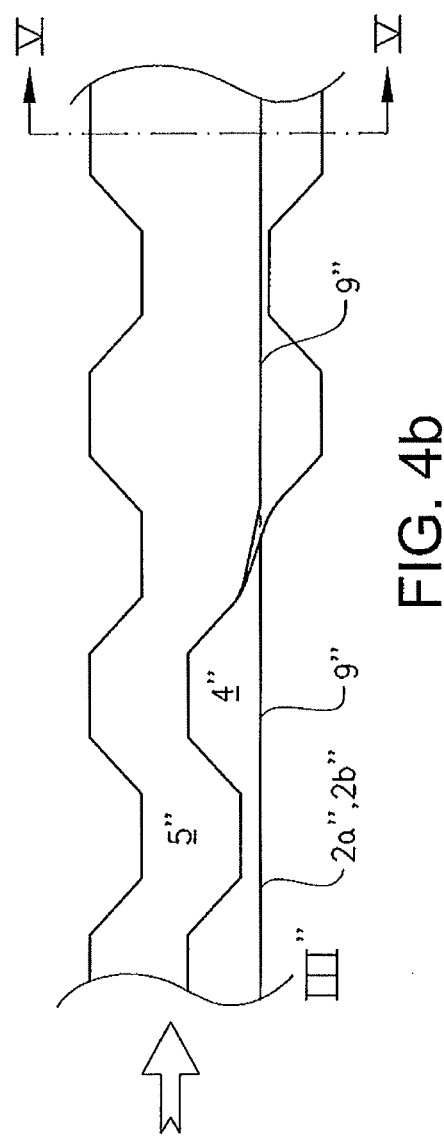
Figure 5:
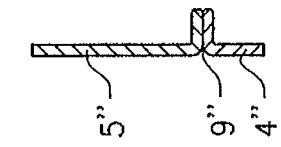

In FIGS. 4a and 4b a third embodiment is schematically shown in plan views similar to FIGS. 1a and 1b. Components similar to corresponding components in FIGS. 1a and 1b are given the same reference numeral with the addition of a bis sign. Also in this embodiment the web 1" a cut 3" identical to cut 3 in FIG. 1a is made dividing web 1" into webs 4",5". The shifting step II" involves a folding 180 degrees of web 4" so that cutting line 3" will be turned away from edge 2b" of web 5", i.e. be directed upwards in FIG. 4a. The web 4" is then longitudinally shifted so that the convex and concave portions of web 4" and web 5" formed by the cutting line 3" will coincidence as illustrated in FIG. 4b. In step III" in FIG. 4b, the edges 2a", 2b" are joined together by gluing, heat welding or with the aid of an ultrasound device. After the joining step, web 4" is folded 180 degrees so that the concave-convex portions of web 4" will be directed in an opposite direction as the concave-convex portions of web 5". The seam 9" created in this embodiment is shown in a sectional view in FIG. 5.

Although the method has been described for the manufacture of a top sheet material it can be used also for the manufacture of a backsheet material having leg openings. Thus, the start material in the first continuous web can be any material known to be used as a top sheet or back sheet material.

If the material manufactured according to embodiments of the present invention is to be wound up on a storage roll before being introduced into a manufacturing line for disposable absorbent articles, the first continuous web 1 can be split into the second and third webs 4,5 along its whole length before being shifted. This is, however, not preferred since a very long conveyer is then needed.

The described embodiment can be modified without leaving the scope of invention, other shifting devices than a shifting conveyer can for example be used. If the web of top sheet material is a weldable material the second and third webs can be joined to each other by a weld seam instead of a glue seam. The lines giving the wave form of the cutting line need not be straight but can for example form a sinus wave. Furthermore, instead of shifting the second web 4, the third web 5 can be shifted. It is also possible to have separate devices for the lateral and longitudinal displacement of web 4 in relation to web 5. A splicing strip for indirectly joining the straight edges of the second and third webs together can be used also if no gap exists between said edges, i.e. when said edges lie edge-to-edge or overlap each other. The present invention should therefore only be limited by the content of the enclosed patent claims.

The invention claimed is:

1. A method of manufacturing a top sheet material or back sheet material for use in the manufacture of disposable absorbent articles comprising the steps of:
    a) splitting a continuous first web of sheet material having substantially straight side edges into a second and third continuous web by a single alternating concave-convex cutting line cut in a longitudinal direction along said continuous first web, said cutting line being distanced from both side edges of said continuous first web;
    b) shifting the second continuous web in a lateral direction in relation to the third continuous web so that the substantially straight edges of the second and third continuous webs are parallel to and adjacent to each other and longitudinally shifting the second continuous web so that the series of concave edge portions and the series of convex edge portions of the second and third continuous webs are longitudinally aligned with each other; and
    c) directly or indirectly joining the straight edges of the second and third continuous webs to each other, thereby forming a composite fourth web,
    wherein the cutting line is made in said first continuous web so that all portions of said cutting line are distanced from a longitudinal centre line of said first continuous web.

2. The method according to claim 1, wherein said cutting line is formed by a repeating series of the following pattern: a straight line—an outwardly inclined line—a straight line—an inwardly inclined line.

3. The method according to claim 1, wherein said first continuous web is made of top sheet material.

4. The method according to claim 1, wherein the straight edges of the second and third webs are overlapping each other after the shifting of the second web.

5. The method according to claim 1, wherein the straight edges of the second and third webs lie edge-to-edge after shifting of the second web.

6. The method according to claim 1, wherein the straight edges of the second and third webs are distanced from each other or lie edge-to-edge after shifting of the second web and are indirectly joined to each other by a splicing strip.

7. The method according to claim 6, wherein the splicing strip forms part of a standing gather.

8. The method according to claim 1, wherein a standing gather is attached to the composite fourth web along the joining line between the second and third webs.

9. The method according to claim 3, wherein the longitudinal centre line of the alternating concave-convex cutting line is distanced from the longitudinal centre line of the first web by 40-120 mm when a top sheet material for an adult diaper is manufactured and by 40-80 mm when a top sheet material for a baby diaper is manufactured.

\* \* \* \* \*